United States Patent [19]

Polk et al.

[11] Patent Number: 4,535,759
[45] Date of Patent: Aug. 20, 1985

[54] ULTRASONIC MEDICAL INSTRUMENT

[75] Inventors: Todd J. Polk, Holland; James F. Morrin, Philadelphia, both of Pa.

[73] Assignee: Cabot Medical Corporation, Langhorne, Pa.

[21] Appl. No.: 431,197

[22] Filed: Sep. 30, 1982

[51] Int. Cl.³ ............................................. A61H 23/00
[52] U.S. Cl. .................................... 128/24 A; 128/343
[58] Field of Search ............... 128/24 A, 303.11, 328, 128/341, 361, 660, 343; 433/119

[56] References Cited

U.S. PATENT DOCUMENTS

| 3,589,363 | 6/1971 | Banko . | |
| 3,792,701 | 2/1974 | Kloz et al. | 128/328 |
| 3,884,239 | 5/1975 | Bucaio . | |
| 3,927,675 | 12/1975 | Pohlman et al. | 128/328 |
| 3,980,906 | 9/1976 | Kuris | 128/24 A |
| 4,013,079 | 3/1977 | Lindemann | 128/341 |
| 4,136,700 | 1/1979 | Broadwin et al. . | |
| 4,169,984 | 10/1979 | Parisi . | |
| 4,249,901 | 2/1981 | Wieser | 433/119 |
| 4,315,514 | 2/1982 | Drewes | 128/24 A |

Primary Examiner—Kyle L. Howell
Assistant Examiner—Francis J. Jaworski
Attorney, Agent, or Firm—Austin R. Miller

[57] ABSTRACT

An ultrasonic friction reducing device is comprised of an ultrasonic generator having a special sweep frequency oscillator, a piezoelectric crystal transducer and a cervical dilator probe. The generator produces an oscillatory electric current for the operation of the device. The piezoelectric crystal transducer converts the oscillatory electric current produced by the generator into a vibratory mechanical motion. The transducer, through mechanical coupling, transmits the ultrasonic energy into the friction reducing probe.

5 Claims, 6 Drawing Figures

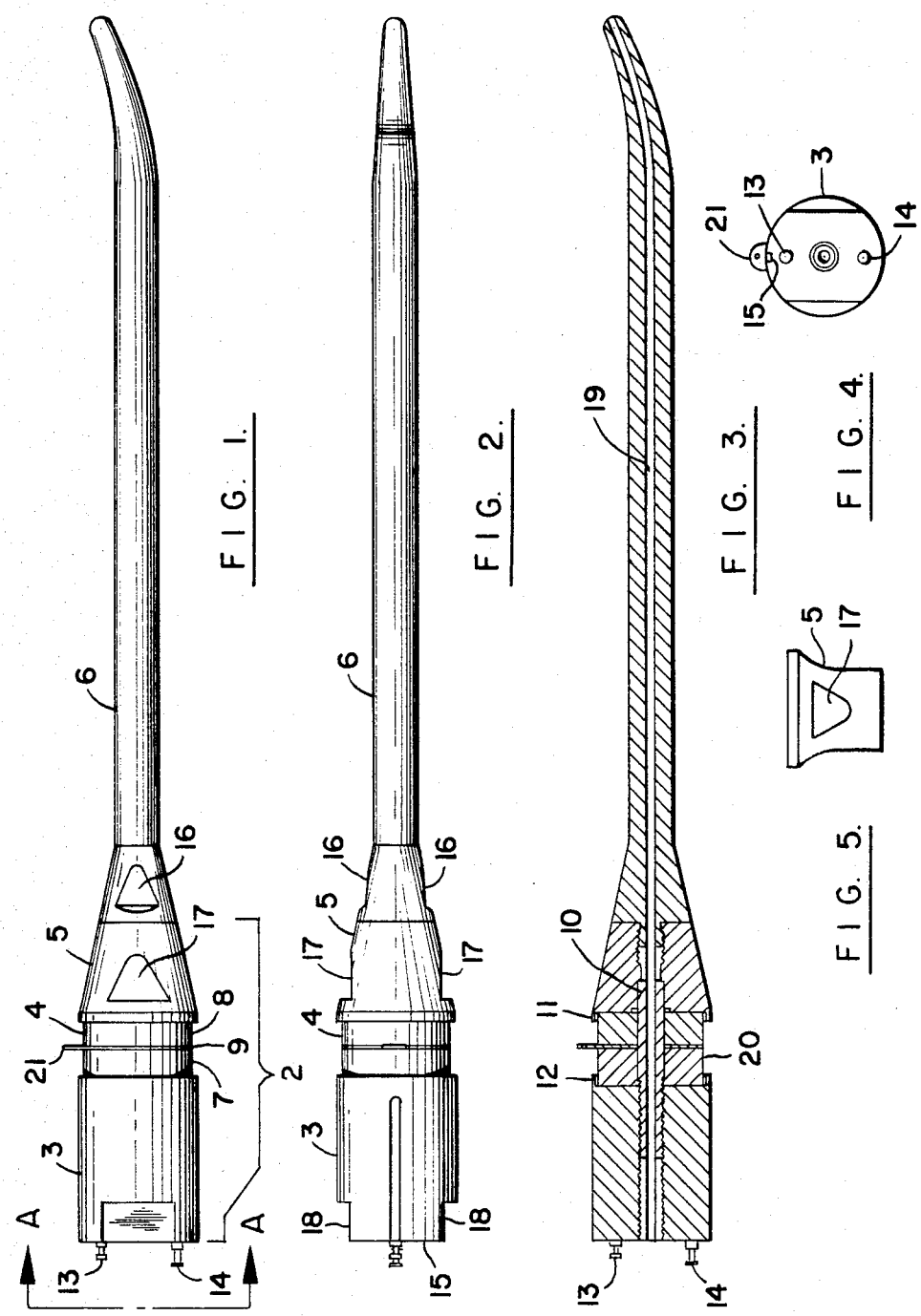

ULTRASONIC MEDICAL INSTRUMENT

BACKGROUND OF THE INVENTION

This invention relates to an ultrasonic system and method for facilitating access of a diagnostic, therapeutic, probing, dilating or manipulating instrument through a body passageway wherein the internal diameter of the body passageway is initially smaller than the external diameter of the instrument. More specifically, this invention relates to an ultrasonic system and method for facilitating dilation of the cervix.

Various surgical devices employing ultrasonic-vibratory means are known in the art. U.S. Pat. No. 4,169,984 discloses an ultrasonic probe for ultrasonically removing material such as in the de-scaling of teeth and pulverizing of cataract tissue. U.S. Pat. No. 4,136,700 discloses an apparatus for use in surgically removing tumorous neurological tissue having a tool tip vibrating in the ultrasonic range, irrigation means and expiration means. U.S. Pat. No. 3,884,239 discloses a tool for use in connection with the introduction of an implant into a mucosa-lined body having a vibrating unit connected with a mucosa-engaging structure for removing a mucosa lining from the interior of the body cavity. U.S. Pat. No. 3,589,363 discloses an instrument having a working operative tip vibrating at high frequencies and with minute amplitudes for breaking apart and removing material such as in the removal of cataracts from the eye.

All of the foregoing references illustrate applications of ultrasound for the purpose of damaging tissue.

An object of the present invention is to provide an ultrasonic system which protects tissue from damage and is uniquely useful for facilitating access of a medical instrument through a body passageway wherein the internal diameter of the body passageway is initially smaller than the external diameter of the instrument.

A further object of the invention is to provide an ultrasonic cervical dilator system using relatively low power as compared to the tissue-destroying illustrations of the prior art, and which is useful for assisting in gentle and tissue-protective dilation of the cervix.

Another object of the invention is to provide an ultrasonic cervical dilator system which generates minimum heat and essentially no tissue injury due to thermal, cavitory or protoplastic streaming effects.

A still further object of the invention is to provide an ultrasonic cervical dilator system which greatly reduces cervical injury which commonly occurs during forcible dilation of the cervix.

BRIEF DESCRIPTION OF THE INVENTION

The preferred form of ultrasonic cervical dilator system, as shown in the appended drawings, is comprised of an ultrasonic generator having a special sweep frequency oscillator, a piezoelectric crystal transducer and a cervical dilator probe. The generator produces an oscillatory electric current for the operation of the system. The piezoelectric crystal transducer converts the oscillatory electric current produced by the generator into a vibratory mechanical motion. The transducer through mechanical coupling transmits the ultrasonic energy to the cervical dilating probe.

The piezoelectric transducer, the coupling mechanism and the probe combine to form a transducer system which transmits the ultrasonic energy in directions both perpendicular and tangential to the tissue of the cervical canal with most of the energy transmitted parallel to the tissue. The mechanical interaction between the probe and cervical tissue is a combination of driving action along the axis of the cervical canal along with gentle compression and decomposition of the wall of the cervix. Means are provided for maintaining the ultrasonic frequency at or near resonant frequency during operation of the system.

It has been found that the interaction between the dilator and cervical tissue reduces the friction of entry of the dilator into the canal by as much as 90 percent or more. This reduction in the friction of entry and the resultant facilitation of entry greatly reduces the possibility of cervical injury, such as small tears of the cervix, lateral cervical perforations and lower uterine perforations, which have commonly occurred during standard forcible dilation of the cervix. The ultrasonic cervical dilator system of the present invention is particularly suited for outpatient screening for endometrial cancer in post-menopausal women where the ultrasonic system facilitates cervical transit in patients having stenosed os.

Other objects and advantages of the present invention will become readily apparent to those skilled in the art from the following detailed description wherein only the preferred embodiment of the invention is shown and described. It should be realized that the invention is capable of other and different embodiments and modifications in various obvious respects may be made without departing from the spirit of the invention. Thus, the drawings and description are to be regarded as illustrative in nature, not as restrictive.

BRIEF DESCRIPTION OF THE DRAWINGS

FIG. 1 is a side view of a preferred embodiment of the ultrasonic device of the present invention.

FIG. 2 is a top view of the embodiment of the invention shown in FIG. 1.

FIG. 3 is a cross-sectional view of the embodiment of the invention shown in FIG. 1.

FIG. 4 is an end view of the embodiment of the invention shown in FIG. 1, taken along the line A—A.

FIG. 5 is a side view of another embodiment of the driver means of the invention.

DETAILED DESCRIPTION OF THE PREFERRED EMBODIMENTS

Figure 6:
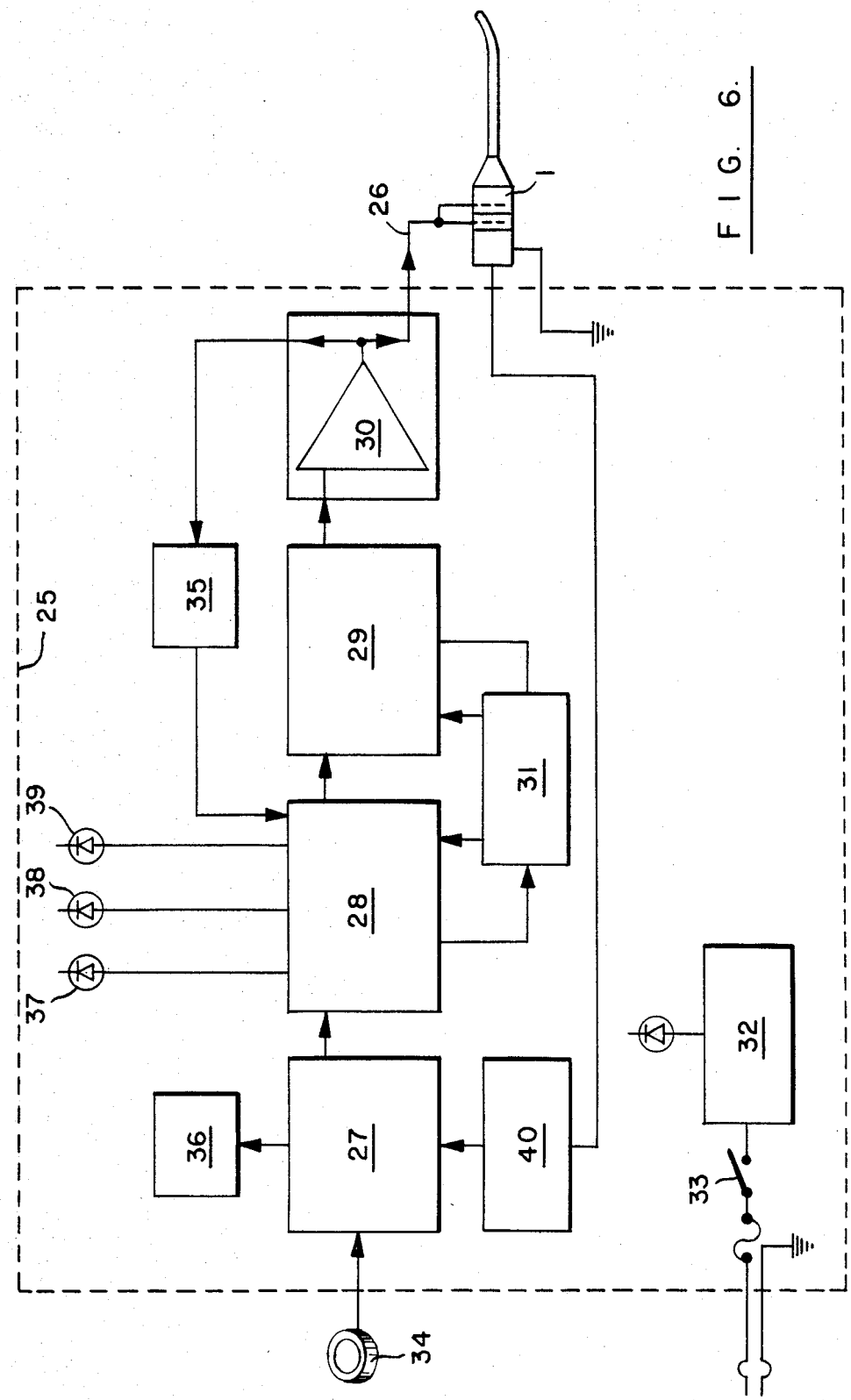
FIG. 6 is a block diagram of a preferred embodiment of the invention.

Referring now to the specific embodiments of the invention shown in the drawings, and turning first to FIGS. 1-5, an ultrasonic device used for facilitating cervical dilation comprises a handle portion 2 containing a back-up member 3, a piezoelectric transducer assembly 4 and a director member 5 which provide ultrasonic vibrations to cervical probe 6. Cervical probe 6 is threadably connected to director member 5. The piezoelectric transducer assembly 4 is comprised of two transducers 7 and 8 which may, for example, be comprised of lead zirconate or ceramic material, positioned positive to positive and joined by a thin contact 9, which may be comprised of copper, and has electrical wire attachment 21. Transducer assembly 4 is slidably fitted on pin 10 extending from director member 5. Back-up member 3 is threadably connected to pin 10 extending from director member 5 such that transducer assembly 4 is located between director member 5 and back-up member 3. Transducer assembly 4 is insulated from pin 10 by insulation. Flanges 11 on director member 5 and flange 12 on back-up member 3 further hold transducer assembly 4 in position. Probe 6, director member 5, and back-up member 3 are provided with flat surface areas 16, 17 and 18, respectively, to facilitate assembly of the device. Ultrasonic device 1 may be provided with a hollow core 19 as shown in FIG. 3 to permit the introduction of therapeutic agents or to allow suction removal of tissue, such as in routine endometrial biopsy procedures. Pins 13 and 14 and slot 15 on back-up member 3 provide means for connecting the ultrasonic device 1 to the ultrasonic generator 25 of the ultrasonic cervical dilator system of FIG. 6.

Turning now to FIG. 6, the ultrasonic generator will be described with reference to the block diagram of FIG. 6. The ultrasonic generator 25 must be connected to an AC power source, not shown, and the piezoelectric crystal transducer 4 must be properly connected to the generator output 26 to operate. The ultrasonic generator is comprised of actuation circuit 27, detector and trigger circuit 28, sweep and oscillator circuit 29, power amplifier circuit 30, ramp generator circuit 31 and DC power supply circuit 32. With the ultrasonic generator plugged in an AC source and the power switch 33 on, the AC current from the source enters the generator 25 and is transformed to a low voltage DC current by DC power supply 32. Four (4) separate DC power supplies are contained within DC power supply 32: a dual+and −15 volt DC power supply for power for the sweep and oscillator circuit 29, and a dual+and −28 volt DC power supply for the power amplifier circuit 30. The ultrasonic generator output is energized when the operator depresses the actuation footpedal 34. With footpedal 34 depressed, a relay in actuation circuit 27 is energized. The relay contacts close initiating operation of the detector and trigger circuit 28. The detector and trigger circuit 28 sends an electric pulse to the electronic logic of the remaining circuits immediately following actuation. This initial electric pulse resets all the logic components to the proper initial state. Concurrently the initial electric pulse is sent to oscillator 29 and ramp generator 31, beginning their operation. Oscillator 29 is a sine wave generator whose initial frequency following actuation is set to about 30 kilohertz. The oscillator output is amplified by the power amplifier 30 and transmitted through the interconnecting cable 26 to the piezoelectric transducer assembly 4. The amplified oscillator output is transformed by the transducer to vibratory mechanical motion. The amplitude of the output current is monitored by feeding back a portion of the amplifier output to the detector and trigger circuit 28 through the automatic frequency sensing circuit 35. The ramp generator 31 controls the output frequency of the voltage controlled oscillator 29. As described previously, when the ultrasonic generator 25 begins operation, the initial oscillator frequency is approximately 30 kilohertz. Immediately following actuation, the output voltage of the ramp generator 31 increases from its initial value of zero. The output voltage of the ramp generator 31 increases linearly versus the amount of actuation time, i.e., the voltage output increases linearly with an increasing amount of actuation time. The frequency of the voltage controlled oscillator 29 decreases as the output voltage from the ramp generator 31 increases. This process continues until the piezoelectric transducer and probe assembly 1 reaches its resonant frequency, which generally is in the range of from about 20 kilohertz to about 30 kilohertz. At resonance, maximum power transfer occurs and maximum efficiency is achieved.

Maximum efficiency of the system is also dependent on the use of the proper coupling torque in assembling ultrasonic device 1. It has been discovered that the operating efficiency increases predictably, in proportion to the torque used to squeeze the crystalline transducers 7 and 8 together when the torque is in the range below about 90 foot-pounds but surprising, at a high torque, in the range of about 90 foot-pounds, the efficiency increases sharply and then levels off when the torque becomes greater than about 100 foot-pounds. Achievement of resonant frequency, generating the maximum mechanical motion with minimum power, prevents development of heat by the unit and minimizes tissue damage. The resonant frequency, the optimum operating frequency, is detected by the automatic frequency sensing circuit 35 which sends an electric pulse to the trigger and detector circuit 28 signaling that the optimum operating frequency has been achieved. The trigger and detector circuit 28 sends an electric pulse to the ramp generator logic control stopping operation of the generator. The ramp generator 31 will hold its present value. Thus, the oscillator output frequency will be set at the initial resonant frequency. The resonant frequency of the piezoelectric transducer and probe assembly, however, varies due to internal heating of the piezoelectric transducer. To compensate for this variation, the sweep generator is incorporated into the system. The sweep generator of circuit 29 is actuated concurrently with the disabling of the generation of the ramp, i.e., when the initial resonant frequency is achieved. The sweep generator of circuit 29 is a frequency modulator and varies the output frequency of the oscillator sinusoidally over a period of time. Thus, the final oscillator output frequency, after achievement of resonance, varies within a small range over a period of time. It has been found through experimentation that the resonant frequency does not generally vary more than about 1.5 kilohertz during operation of ultrasonic generator 25. Thus, after the automatic frequency sensing circuit 35 has detected the initial resonance frequency, the final oscillator output frequency is varied from the initial resonance value by the sweep generator of circuit 29 over a plus and minus range of about 1.5 kilohertz. For example, if maximum power transfer and initial resonance occurs at 25 kilohertz, the output frequency of the power amplifier will vary from 23.5 to 26.5 kilohertz.

Thus, an important feature and advantage of this invention is attained since it is insured that the piezoelectric transducer and probe assembly is operated near or at resonant frequency.

Other features of the system are as follows. An audible alarm 36 indicates when resonance has been achieved. There is also a visual indication of actuation provided by the power probe indicator 37. When the automatic frequency tuning circuitry is searching for the power resonant frequency, the standby indicator 38 is turned on telling the operator not to use the device. When the automatic frequency circuitry has found the correct resonant frequency, the standby indicator 38 is turned off and the ready indicator 39 is turned on. For maximum safety in operation, the ultrasonic generator should be fully isolated. It is then suitable for use with electrically susceptible patients when operated from an AC power source. The line frequency electrical leakage current can be minimized through the design and selection of components with minimal capacitance coupling, as is well known to those skilled in the art. A ground fault detector circuit 40 may be incorporated into the design of the ultrasonic generator. Such a circuit ensures that the piezoelectric transducer is connected to ground (earth) and continuously checks the integrity of the grounding circuit. With such a circuit, the generator will not operate when the transducer assembly is not grounded properly, providing protection from electrical shock for the patient and the physician.

While the present invention is herein described in terms of a cervical dilator probe, it is, of course, apparent that the device of the invention may be adapted for use at any body passageway such as the urethra, anus and other passageways.

While the foregoing description refers to specific circuitry for achieving and maintaining a resonant frequency, it will be appreciated that many other circuits may be devised and used. It is important and advantageous, however, to be able to tune each driver automatically to its resonance point, allowing the physician easily to control amplitude and to minimize the temperature rise of the dilator probe during the period of its use.

It is also advantageous to provide a quick-acting means for tightly coupling the driver and probe with about the same torque each time, since loose driver-probe connections tend to produce excessive heat with resultant patient discomfort.

EXAMPLE

The following specific example demonstrates the specific steps taken by a physician using a preferred embodiment of the ultrasonic system of the present invention for cervical dilation. The patient is placed in the lithotomy position. The vagina and perineum are antisepticized with a solution such as a providone-iodine (Betadine) and alcohol solution. The cervix is grasped with an appropriate tenaculum and the cervix is gently drawn to the outlet. The position of the uterus is determined by usual bi-manual examination. Standard Hegar dilator and uterine sounds are utilized without force to determine the smallest diameter dilator which meets cervical resistance. The dilator corresponding to that diameter is chosen for initial entry. The dilator is attached to the driver member portion of the ultrasonic device as shown in FIG. 1. The system is tuned to resonance by the ultrasonic generator. With the dilator operationally optimal, the physician introduces the dilator into the cervical os. The dilator is rotated to the proper direction for the angular position of the uterus. The dilator is advanced into the os as far as possible with gentle force along with adjunctive ultrasound vibration until any unusual change in resistance is noted. If cervical resistance increases, a blind pathway is suspect. The dilator is withdrawn and flexure of the uterus reevaluated with a smaller dilator or sound. The dilator may then be reintroduced into the cervical os at the proper direction for the flexure of the uterus. When cervical resistance decreases at a depth of penetration judged sufficient for passage of the internal os, the dilation can be further pursued with the next larger dilator if required.

The following is claimed:

1. An ultrasonic medical instrument for providing access to an interior portion of a body comprising the combination of:
   a. an elongated probe adapted to be introduced into the body;
   b. an ultrasonic driver adapted to vibrate the probe along its longitudinal axis at an ultrasonic frequency, whereby the vibration applied to the probe reduces friction between the probe and the body, said driver comprising a back-up piece, a pair of piezo-electric transducers separated by an electrical conductor and arranged positive to positive, a director, and means for compressing said back-up piece, transducers and director into intimate contact with each other,
   c. a frequency regulator connected for maintaining the vibration frequency of the instrument at or near the resonant frequency of the instrument, said regulator including an automatic frequency sensing circuit connected and arranged to detect the resonant frequency of the probe, and means responsive to a signal from said circuit to bring the instrument to its resonant frequency; and
   d. means forming a hollow core extending lengthwise through all of said back-up piece, transducers, director and probe to permit the introduction of therapeutic agents or the application of suction through the probe.

2. The instrument of claim 1, wherein the resonant frequency of the instrument is in the range of from about 20 kHz to about 30 kHz.

3. The instrument of claim 1, wherein the two transducers are urged together at a torque of about 90 to 100 ft-lbs.

4. The instrument of claim 1, wherein the back-up piece, transducers and director have hollow cores and are mounted upon a common pin.

5. The instrument of claim 4, wherein insulation is provided between the transducers and the pin.

* * * * *